United States Patent
Jung et al.

(10) Patent No.: US 9,285,340 B2
(45) Date of Patent: Mar. 15, 2016

(54) METHODS FOR SEPARATING PARTICLES AND/OR NUCLEIC ACIDS USING ISOTACHOPHORESIS

(75) Inventors: Byoungsok Jung, San Jose, CA (US); Kevin Ness, San Mateo, CA (US); Klint A. Rose, Alviso, CA (US)

(73) Assignee: Lawrence Livermore National Security, LLC

(*) Notice: Subject to any disclaimer, the term of this patent is extended or adjusted under 35 U.S.C. 154(b) by 1157 days.

(21) Appl. No.: 12/542,215

(22) Filed: Aug. 17, 2009

(65) Prior Publication Data

US 2011/0036718 A1  Feb. 17, 2011

(51) Int. Cl.
*G01N 27/447* (2006.01)

(52) U.S. Cl.
CPC .... *G01N 27/44747* (2013.01); *G01N 27/44773* (2013.01)

(58) Field of Classification Search
CPC .......... G01N 27/447; G01N 27/44747; G01N 27/44773; G01N 2030/8827; B01D 57/00
USPC .................................................. 204/549, 645
See application file for complete search history.

(56) References Cited

U.S. PATENT DOCUMENTS

| 6,090,251 | A * | 7/2000 | Sundberg et al. | 204/453 |
| 7,223,325 | B2 * | 5/2007 | Landers et al. | 204/453 |
| 2010/0224494 | A1 * | 9/2010 | Chambers et al. | 204/549 |

FOREIGN PATENT DOCUMENTS

WO    WO2008/053047    *    5/2008    ........... G01N 27/447

OTHER PUBLICATIONS

Fu, Jianping et al., "A patterned anisotropic nanofluidic sieving structure for continuous-flow separation of DNA and proteins" Nature Publishing Group, Published online: Feb. 5, 2007 www.nature.com/naturenanotechnology.
Janasek, Dirk et al., "Isotachophoresis in Free-Flow Using a Miniaturized Device", Analytical Chemistry, vol. 78, No. 11, Jun. 1, 2006; American Chemical Society, 2006, p. 3815-3819.
Prest, Jeff E. et al., "Miniaturised isotachophoresis of DNA" Journal of Chromatography A, 1156 (2007) p. 154-159 www.elsevier.com/locate/chroma.
Jung, Byoungsok et al., "On-Chip Millionfold Sample Stacking Using Transient Isotachophoresis" Analytical Chemistry, vol. 78, No. 7, Apr. 1, 2006, p. 2319-2327.
Santiago, Juan G. et al., "Stanford Microfluidics Lab" http://microfluidics.stanford.edu.

(Continued)

*Primary Examiner* — Luan Van
*Assistant Examiner* — Gurpreet Kaur
(74) *Attorney, Agent, or Firm* — Zilka Kotab (57) ABSTRACT

According to one embodiment, a method includes co-feeding fluids comprising a leading electrolyte, a trailing electrolyte, and at least one of DNA and RNA to a channel, and applying an electric field to the fluids in a direction perpendicular to an axis of the channel for inducing transverse isotachophoresis. In another embodiment, a method includes co-feeding fluids to a channel. The fluids include a leading electrolyte, a trailing electrolyte, biological objects, at least one of DNA and RNA, and a spacer electrolyte having an electrophoretic mobility that is between an electrophoretic mobility of at least some of the biological objects and an electrophoretic mobility of the at least one of the DNA and the RNA. The method also includes applying an electric field to the fluids in a direction perpendicular to an axis of the channel for inducing transverse isotachophoresis. Other methods of isotachophoresis are disclosed in addition to these.

20 Claims, 4 Drawing Sheets

(56) References Cited

OTHER PUBLICATIONS

Wagner, H., "Free-flow electrophoresis," 1989 Nature Publishing Group, Nature, vol. 341, Oct. 19, 1989, pp. 669-670.

Eisenbarth, George S., "Application of Monoclonal Antibody Techniques to Biochemical Research," 1981 Academic Press, Inc., Analytical Biochemistry, vol. 111, p. 1-16.

* cited by examiner

METHODS FOR SEPARATING PARTICLES AND/OR NUCLEIC ACIDS USING ISOTACHOPHORESIS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to separation and/or purification of fluids in MEMS (and/or chip-based)- and capillary-based systems, and more particularly, to methods for separating particles and/or nucleic acids from other fluid constituents using isotachophoresis.

BACKGROUND

Bioengineered and emerging pathogens represent a significant threat to human health. The best defense against a rapidly-expanding pandemic is to have capabilities to isolate the causative pathogen quickly from biological samples such that it can be characterized and so that tests and vaccines can be developed against it. Whether the scenario for biological analysis involves samples from the environment, food, water, agriculture, animals, or from humans, the one persistent technology gap in the process of identifying and quantifying the presence of pathogenic agents has been "the front end of assays," namely sample handling and sample preparation.

One problem encountered in sample handling is separating and concentrating small particles from complex liquid samples. This problem is of particular importance in the applications of pathogen detection and medical diagnostics, wherein separating a particle type of interest (e.g., cells, viruses, bacteria, etc.) from an obscuring background of other materials can increase the sensitivity of a diagnostic assay, and allow particles present at very low concentrations to be detected more easily. Some prior approaches have been based on passive separations relying upon differences in diffusion speeds of different particles or the ability of different particles to negotiate an array of small obstacles or openings. Simple physical filters can be included in this category.

Other approaches have used centrifugal motion to manipulate particles and drive them to separate locations, which has its advantages and disadvantages. The basic slowness and awkwardness of centrifugation is a primary problem with this sample preparation technique, but also its incompatibility with automation or high-throughput parallel processing causes this technique to suffer in the application of rapid virus and biothreat detection systems. It relies on bulky equipment and requires manual manipulation by a technician. It can also be dangerous as the high rotational speeds developed within ultracentrifuges can result in serious accidents if the equipment fails, potentially spreading aerosolized virus over a large area. Many laboratories that work with pathogenic viruses prohibit or limit the use of centrifuges for this reason.

Most standard laboratory methods for viral separation from oral-cavity samples consist of batch procedures based on centrifugation or week-long propagation of viruses. Three critical drawbacks to these techniques are: 1) clinical labs avoid ultracentrifugation of pathogenic samples due to the possibility of aerosolization of the sample (especially following potential equipment failure, as previously stated); 2) all the viruses are coalesced and further processing is required to isolate the pathogen; and 3) these techniques are not amenable to quick, high-throughput processing, which may be necessary to correctly identify the pathogen in a timely fashion.

Separation and purification of viruses from clinical samples that consist of free floating nucleic acids, viruses, bacteria, cells, debris, and/or mucus in isotonic solutions is of particular interest in the identification of potential bio-threats. The approaches to identify potential bio-threats include acoustic focusing of large (>2 um.) particulates, electrophoresis of charged biological particles and molecules, and dielectrophoresis of bacteria. However, none of these can selectively exclude exogenous free-floating nucleic acids, which might hinder amplification and identification of nucleic acids of the target viruses. Adding DNAse or RNAse in the buffer is not effective, as it inhibits PCR process and currently cannot be inactivated in a reliable manner.

The state-of-art nucleic acids purification methods mainly rely on mechanical and/or affinity-based filtration. These conventional methods require long processing times (~20 min) and relatively expensive reagents (e.g., magnetic microbeads and antibodies), are traditionally difficult to implement in microchip systems, and/or using the Boom capture chemistry, the conventional methods require reagents that may possibly lyse viruses and expose the viruses' internal DNA to the DNA extraction process.

As is true in any such biodetection process, sample preparation is a critical requirement for many biological assays and is a major bottleneck in the process of detecting and identifying biological agents. Capabilities for separation, detection, and classification of unknown species from biological samples becomes more urgent when dealing with bioengineered threats because the investigator must rapidly isolate the unknown from all the other particles in the sample to enable characterization and the development of antibody or nucleic acid-based detection assays. Viruses are an important category of pathogens because some of its members, such as influenza and smallpox, are extremely infectious and very virulent forms could result in sudden, massive pandemics. Viruses are often difficult to isolate due to their small size (typically <200 nm.), compared with the bulk of the particles in a sample. Therefore, since standard laboratory methods cannot rapidly and efficiently separate or purify virus and bacteria from samples, there is an unaddressed need of national importance in rapid isolation, detection, and classification of engineered and naturally-occurring emerging bio-threats.

SUMMARY

According to one embodiment, a method includes co-feeding fluids comprising a leading electrolyte, a trailing electrolyte, and at least one of DNA and RNA to a channel, and applying an electric field to the fluids in a direction perpendicular to an axis of the channel for inducing transverse isotachophoresis.

In another embodiment, a method includes co-feeding fluids to a channel. The fluids include a leading electrolyte, a trailing electrolyte, biological objects, at least one of DNA and RNA, and a spacer electrolyte having an electrophoretic mobility that is between an electrophoretic mobility of at least some of the biological objects and an electrophoretic mobility of the at least one of the DNA and the RNA. The method also includes applying an electric field to the fluids in a direction perpendicular to an axis of the channel for inducing transverse isotachophoresis.

Other aspects and embodiments of the present invention will become apparent from the following detailed descrip-

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

Figure 1A:
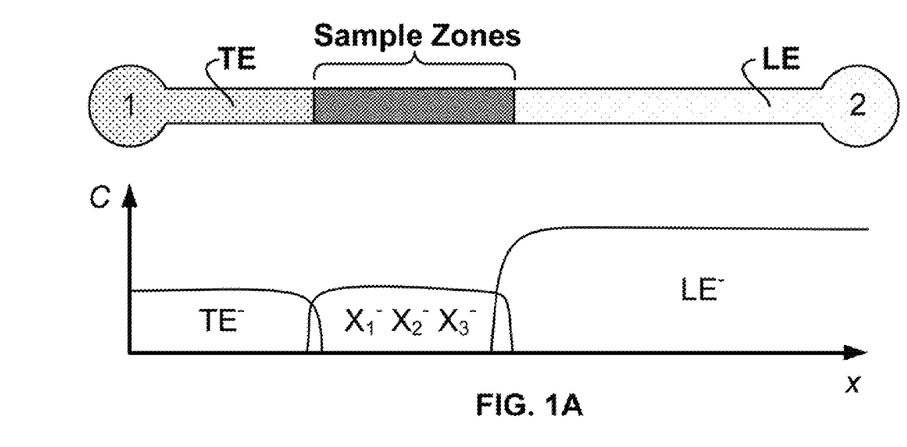
FIG. 1A is a schematic diagram of an initial condition in an isotachophoresis process, according to one embodiment.
Figure 1B:
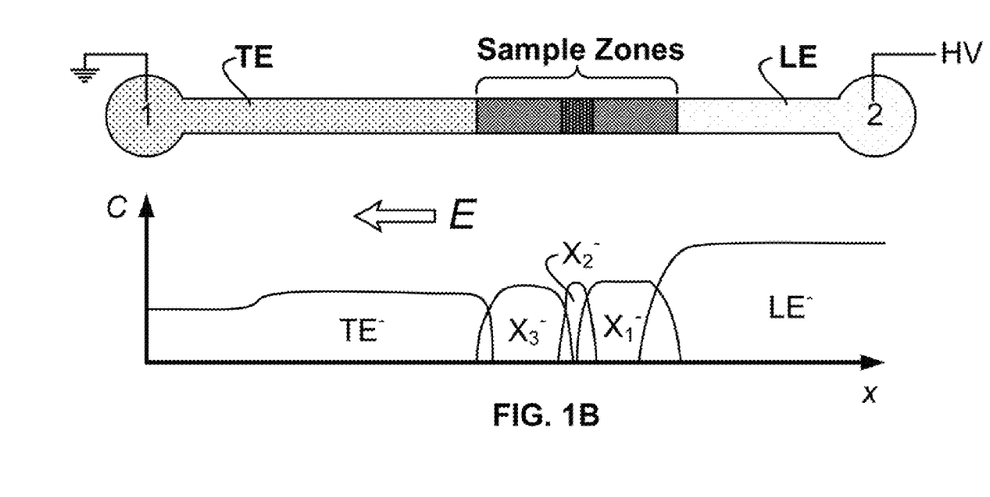
FIG. 1B is a schematic diagram of voltage being applied across the channel in an isotachophoresis process, according to one embodiment.

As used herein, the term isotachophoresis (ITP) refers to an electrophoretic separation (and/or preconcentration) technique that leverages a heterogeneous buffer system of disparate electrophoretic mobilities. In parallel isotachophoresis, presented here by way of illustrating the general concept of isotachophoresis, a plug of fluid containing sample ions to be focused and separated may be introduced between a leading and a trailing electrolyte (LE and TE) whose mobilities are respectively higher and lower than any of the mobilities of sample molecules included in the sample fluid, as shown in FIG. 1A. Under the application of an electric field (E, FIG. 1B) across the electrolyte boundaries in a direction parallel to the direction of the flow of the bulk of the fluid, the sample ions separate and redistribute themselves in contiguous zones in order of reducing dynamically pH-averaged electrophoretic mobility starting from LE to TE, as shown in FIG. 1B., e.g., each sample ion ($X_1^-, X_2^-, X_3^-$, etc.), is focused into its respective, mobility-dependent focal point. At steady state, these focused sample zones migrate at a same speed as that of the leading zones, hence the name "iso-tacho-phoresis." Parallel isotachophoresis, however, has proven to be troublesome in many respects, including the inherent limitations in the required batch processing, as well as the difficulty in removing the sample from the fluids exiting the chamber.

Some inherent preconcentration effects of ITP maintain sharp concentration boundaries between adjacent sample zones, according to some approaches. Away from the diffused boundary regions between the sample zones, the sample concentration may be about uniform and sample concentration in each zone may be obtained using species conservation equations and an electroneutrality condition. The simple ITP system shown in FIG. 1 may be used as an example. FIG. 1 is a schematic of the steps involved in a typical anionic ITP process. According to some approaches, the capillary, channel, etc., is filled with a leading electrolyte LE using pressure driven flow followed by sequential injection of the sample electrolyte and trailing electrolyte TE. High voltage is applied across the capillary, channel, etc., and an electric field is setup inside the capillary, channel, etc., initiating separation of the Sample Zones and achieving an ITP condition.

Figure 2A:
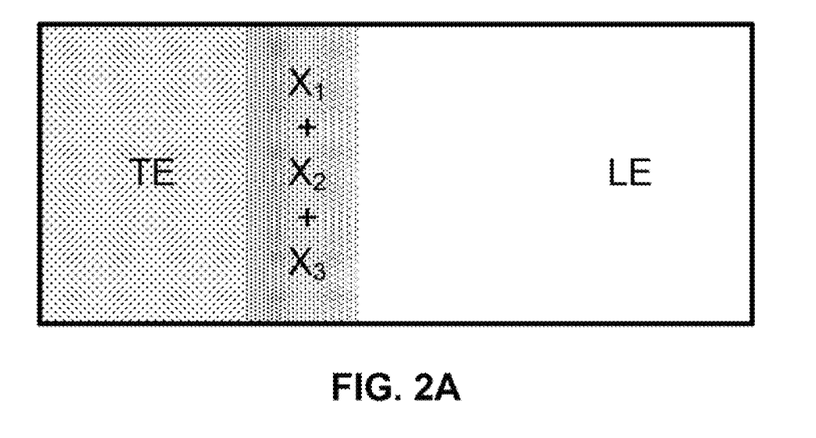
FIG. 2A shows a schematic diagram of an initial condition in an isotachophoresis process, according to one embodiment.
Figure 2B:
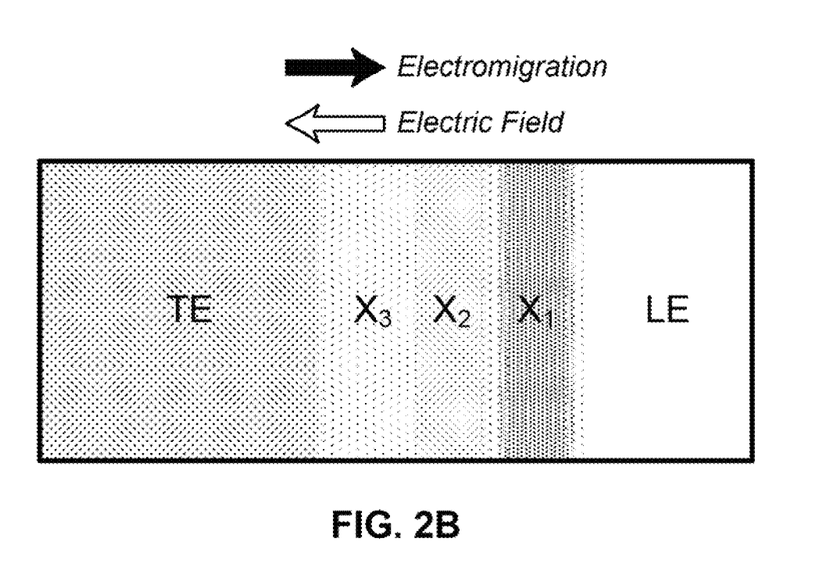
FIG. 2B shows a schematic diagram of an electric field applied across the container in an isotachophoresis process, according to one embodiment.

Referring to FIGS. 2A and 2B, also showing parallel ITP, a plug of sample ions ($X_1, X_2, X_3$, etc.) may be injected between a leading electrolyte LE and a trailing electrolyte TE, with a common counter ion (A, not shown) present everywhere. In this example, electroosmotic flow is fully suppressed to negligible levels. After sufficient focusing time, the various zones in the system will develop locally uniform concentrations (concentration "plateaus" around their respective focal points) where diffusive fluxes are locally insignificant. For this long-time condition, the species conservation equations can be simplified to obtain the well-known Kohlrausch regulating function (KRF) given by Equation 1.

$$\left(\sum_i \frac{C_i}{v_i}\right) = f(x) \qquad \text{Equation 1}$$

where $C_i$ and $v_i$ are the concentration and the electrophoretic mobility of species i, at axial location x in the channel. The constant (in time) function $f(x)$ is governed by the initial condition. This relation can be stated as follows, the sum of concentration-to-mobility ratio of all species at a given location in the channel (relative to the channel wall at negligible electroosmosis conditions) remains invariant with time. Using the KRF Equation (Equation 1), the following expression (Equation 2) can be derived to obtain the concentration adjustment between the two zones assuming no dispersions and bulk fluid velocity.

$$C_X = C_L \frac{v_X(v_L - v_A)}{v_L(v_X - v_A)} \qquad \text{Equation 2}$$

where $C_X$ is the concentration of species X, $C_L$ is the concentration of the leading electrolyte LE, is the electrophoretic mobility of the leading electrolyte, $v_X$ is the electrophoretic mobility of the species X, and $v_A$ is the electrophoretic mobility of the counter ion. Here, the adjusted sample concentration of the species X, $C_X$, is strictly a function of the LE concentration and electrophoretic mobilities in this non-diffuse ID model. After an electric field is applied to the fluids in the channel, the fluids may separate by electrophoretic mobility, as shown in FIG. 2B.

In one general embodiment of the present invention, a method includes co-feeding fluids comprising a leading electrolyte, a trailing electrolyte, and at least one of DNA and RNA to a channel; and applying an electric field to the fluids in a direction perpendicular to an axis of the channel for inducing transverse isotachophoresis.

In another general embodiment, a method includes co-feeding fluids to a channel, the fluids comprising a leading electrolyte; a trailing electrolyte; biological objects; at least one of DNA and RNA; and a spacer electrolyte having an electrophoretic mobility that is between an electrophoretic mobility of at least some of the biological objects and an electrophoretic mobility of the at least one of the DNA and the RNA. The method also includes applying an electric field to the fluids in a direction perpendicular to an axis of the channel for inducing transverse isotachophoresis.

Figure 3A:
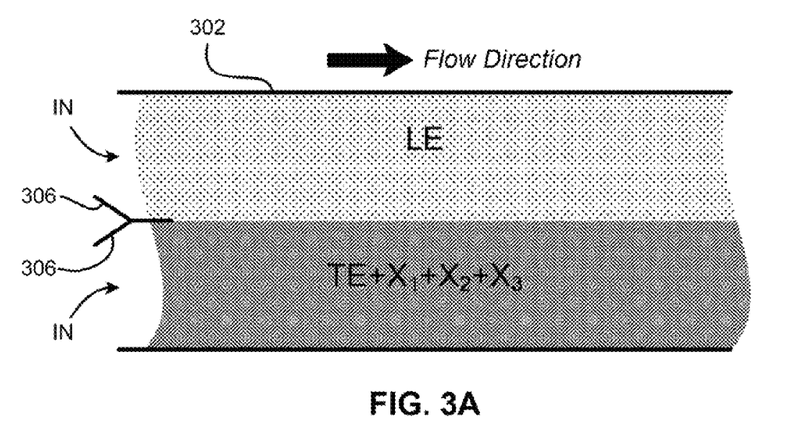
FIG. 3A shows a schematic diagram of an initial condition in a transverse isotachophoresis process, according to one embodiment.
Figure 3B:
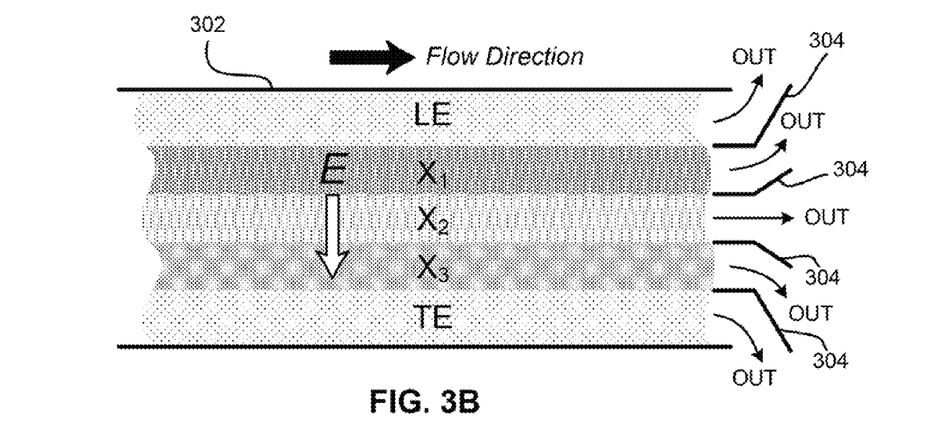
FIG. 3B shows a schematic diagram of an electric field being applied across the channel in a transverse isotachophoresis process, according to one embodiment.

The previous discussion of parallel ITP may be distinguished from the following discussion of transverse ITP. A transverse ITP system may use pressure-driven flows to transfer bulk fluids and an electric filed applied perpendicular to the direction of bulk fluids to separate (and/or preconcentrate) sample constituents. Referring to FIGS. 3A and 3B, schematic diagrams representing some of the steps involved in a transverse ITP system according to one embodiment, the process may be explained in more detail.

Referring to FIG. 3A, two or more streams may respectively contain the leading electrolyte LE and a mixture of the trailing electrolyte TE and sample electrolytes, and may be introduced in a channel 302 by pressure-driven flows. Now referring to FIG. 3B, an electric filed may be applied perpendicular to the axial direction of the channel 302, prompting the ITP process. At a point downstream of the channel 302, sample ions may be separated from the bulk fluid based on their electrophoretic mobilities.

According to preferred embodiments, the transverse ITP system may offer high-throughput sample preparation as the amount of sample to be processed is not limited by an initial confined sample plug as in a traditional, parallel ITP system. This method may also be integrated with other sample preparation modes (such as acoustic focusing) without modification of the design of the H-filter type microchips.

In cases where DNA and/or RNA is to be separated from other constituents in a sample fluid, the transverse ITP system may isolate DNAs/RNAs from the mixture of viruses, cells, and other electrolytes due to the electrophoretic mobility of DNA/RNA being nearly constant regardless the size of the DNA/RNA under same pH and temperature conditions.

The electrophoretic mobility of DNA in free-solution (i.e., without a sieving matrix) is nearly constant regardless of the numbers of base pairs under the same pH and temperature. Therefore, with careful selection of electrolytes (TE, LE, etc.) and a knowledge of electrophoretic mobilities of target viruses and nucleic acids, isotachophoresis may provide an efficient, filter-free DNA/RNA exclusion and/or purification method.

With reference to FIGS. 3A and 3B, a method may be described according to one embodiment. The method includes co-feeding fluids to a channel 302, as shown in FIG. 3A. The length of the channel, width of the channel, shape of the channel, etc., may be selected depending on processing parameters, such as amount of fluids to be processed, time allowed to process, temperature, pressure, etc. In one embodiment, the fluids comprise a leading electrolyte LE, a trailing electrolyte TE, and at least one of DNA and RNA ($X_1, X_2, X_3$, etc.). Now referring to FIG. 3B, an electric field (E) is applied to the fluids in a direction perpendicular to an axis of the channel (where the axis of the channel is about parallel to the direction of flow through the channel, as indicated by the Flow Direction Arrow) for inducing transverse isotachophoresis (ITP). The effect that the transverse ITP has on the fluids is represented by the separation of fluids shown in FIG. 3B. In this representation, the samples ($X_1, X_2, X_3$, etc.) have been separated according to their electrophoretic mobilities. By including post-processing stream separation techniques to this fluid flow channel 302, the separate samples (including DNA and/or RNA) may be isolated for further analysis/identification thereof.

As shown in FIG. 3A, and equally applicable to all embodiments described herein, there may be inlet channels 306 according to one embodiment, which may help in delivering fluids to the channel 302 from separate containers, tanks, vessels, etc., such that the fluids which are to be introduced to the channel 302 may be premixed, isolated, combined, etc., to achieve a desired fluid composition prior to introduction thereof to the channel 302.

In addition, as shown in FIG. 3B, and equally applicable to all embodiments described herein, there may be outlet channels 304, which may help in separating and/or isolating fluid flows once separation has been achieved through transverse ITP, as described herein. There may be a number of outlet channels 304 which is equal to the amount of fluids to be separated, or there may be additional separation processing downstream of the outlet channels 304, such that two or more objects may be fed through an outlet channel prior to final separation. Of course, any device and/or method may be used to introduce and extract the fluids from the channel 302, and the embodiments described above are for reference only and not meant to be limiting in any manner.

According to some approaches, the trailing electrolyte TE may be co-fed to the channel 302 in a mixture with the at least one of the DNA and the RNA. Alternatively, the trailing electrolyte TE may be co-fed to the channel 302 separately from the fluid having the at least one of the DNA and the RNA.

In some embodiments, a bulk of the leading electrolyte LE may be spatially separated from the at least one of the DNA and the RNA upon introduction thereof to the channel 302. For example, more than about 50% of the leading electrolyte LE may be in a remote proximity from the at least one of the DNA and the RNA. Of course, as the fluid flows in the channel 302, this spatial separation may be improved, depending upon processing and channel conditions in the flow direction.

According to some approaches, the fluids may be co-fed to the channel 302 under a pressure higher than atmospheric pressure, such as to create a pressure gradient across the fluids as they flow. In addition, this pressure gradient may cause, at least in part, the fluids to flow from a condition of higher pressure, toward a condition of lower pressure. An alternative method to create this pressure gradient is to apply a vacuum to the outlet(s) of the channel 302, the outlet(s) being downstream from one or more inlet(s). Of course, any other method of forming this pressure gradient may also be used, and these examples are not meant to be limiting. In further approaches, gravity may be used to create the flow through the channel 302.

In some preferred embodiments, the method may further include co-feeding a spacer electrolyte having an electrophoretic mobility that is between an electrophoretic mobility of the leading electrolyte LE and an electrophoretic mobility (such as an average, mean, measured, lowest, highest, etc., electrophoretic mobility) of the at least one of the DNA and the RNA. Since there may be more than one DNAs and/or RNAs present in the sample fluids, an electrophoretic mobility may be calculated, in any number of ways, in order to choose a spacer electrolyte with an electrophoretic mobility that is suitable for separation of the fluids. In this way, the spacer electrolyte may position itself in between the DNA and/or RNA and the leading electrolyte LE. This may enable easier separation of the DNA and/or RNA from the leading electrolyte LE.

In some more preferred embodiments, the method may further include co-feeding a spacer electrolyte having an electrophoretic mobility that is between an electrophoretic mobility of the trailing electrolyte TE and an electrophoretic mobility (such as an average, mean, measured, lowest, highest, etc., electrophoretic mobility) of the at least one of the DNA and the RNA. In this way, the spacer electrolyte may position itself in between the DNA and/or RNA and the trailing electrolyte TE. This may enable easier separation of the DNA and/or RNA from the trailing electrolyte TE.

In some more approaches, the method may include co-feeding a first spacer electrolyte having an electrophoretic mobility that is between an electrophoretic mobility of the leading electrolyte LE and an electrophoretic mobility (such as an average, mean, measured, lowest, highest, etc., electrophoretic mobility) of the at least one of the DNA and the RNA and co-feeding a second spacer electrolyte having an electrophoretic mobility that is between an electrophoretic mobility of the trailing electrolyte TE and the electrophoretic mobility (such as an average, mean, measured, lowest, highest, etc., electrophoretic mobility) of the at least one of the DNA and the RNA. In this way, the leading electrolyte LE may be more easily separated from the DNA and/or RNA, and the trailing electrolyte TE may be more easily separated from the DNA and/or RNA.

According to more approaches, a spacer electrolyte having an electrophoretic mobility that is between an electrophoretic mobility (such as an average, mean, measured, lowest, highest, etc., electrophoretic mobility) of at least some biological objects in one of the fluids and an electrophoretic mobility (such as an average, mean, measured, lowest, highest, etc., electrophoretic mobility) of the at least one of the DNA and the RNA may be co-fed into the channel 302. This spacer layer may be used to make separation of the at least some biological objects from the DNA and/or RNA that is present in the sample fluids. The biological objects, in some approaches, may be selected from a group consisting of viruses, bacteria, and cells. Of course, other biological objects may also be used in conjunction with the methods described herein.

Figure 4A:
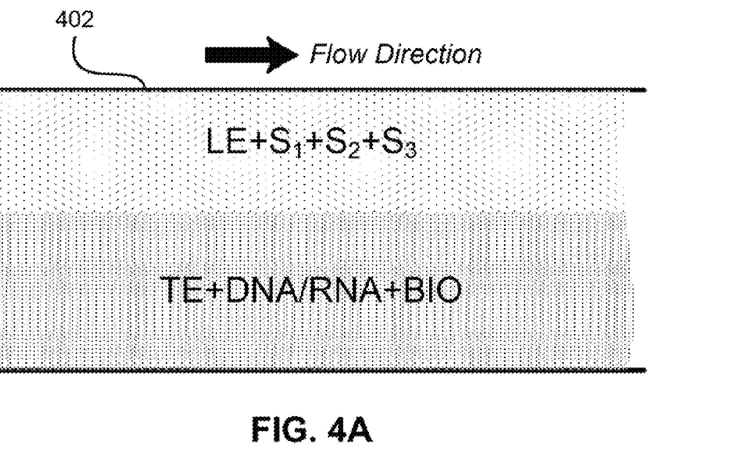
FIG. 4A shows a schematic diagram of an initial condition in a transverse isotachophoresis process, according to one embodiment.

Now referring to FIG. 4A, in one preferred embodiment, the method may further include co-feeding a first spacer electrolyte $S_1$ having an electrophoretic mobility that is between an electrophoretic mobility of the leading electrolyte LE and an electrophoretic mobility (such as an average, mean, measured, lowest, highest, etc., electrophoretic mobility) of the at least one of the DNA and the RNA (DNA/RNA). Also, the method may include co-feeding a second spacer electrolyte $S_2$ having an electrophoretic mobility that is between an electrophoretic mobility of the trailing electrolyte TE and the electrophoretic mobility (such as an average, mean, measured, lowest, highest, etc., electrophoretic mobility) of the at least one of the DNA and the RNA (DNA/RNA). In addition, the method may include co-feeding a third spacer electrolyte $S_3$ having an electrophoretic mobility that is between an electrophoretic mobility (such as an average, mean, measured, lowest, highest, etc., electrophoretic mobility) of at least some biological objects BIO in one of the fluids and the electrophoretic mobility (such as an average, mean, measured, lowest, highest, etc., electrophoretic mobility) of the at least one of the DNA and the RNA (DNA/RNA).

Figure 4B:
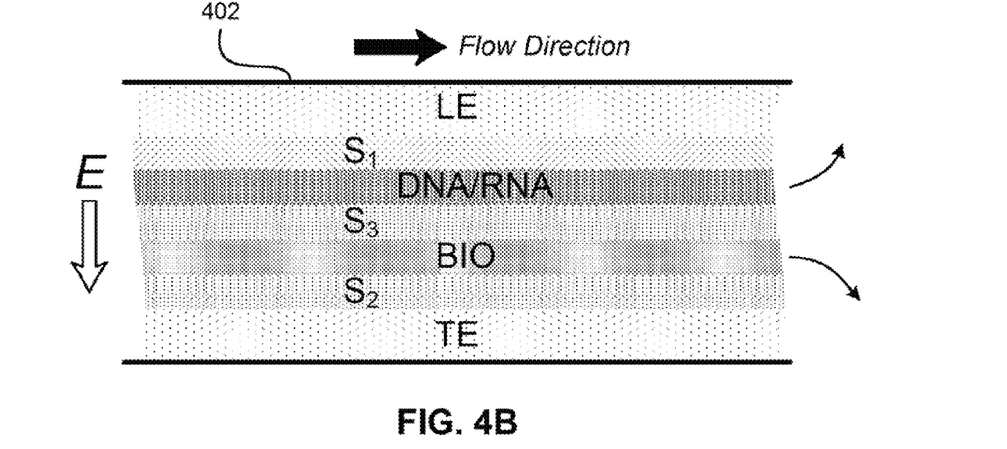
FIG. 4B shows a schematic diagram of an electric field being applied across the channel in a transverse isotachophoresis process, according to one embodiment.

Upon application of an electric field (E), the fluids may separate approximately as shown in FIG. 4B, with the first spacer electrolyte $S_1$ separating the leading electrolyte LE from the DNA and/or RNA (DNA/RNA). Also, the second spacer electrolyte $S_2$ may separate the trailing electrolyte TE from the DNA and/or RNA (DNA/RNA), and the third spacer electrolyte $S_3$ separating the biological objects BIO from the DNA and/or RNA (DNA/RNA).

Since electrophoretic mobility is a key factor in separation capabilities in an ITP system, Table 1 includes the electrophoretic mobility values of illustrative ions, fluorophores, and microbiological samples, as an example.

TABLE 1

Electrophoretic Mobility Values

| | $v\ (10^{-8}\ m^2/Vs)$ |
|---|---|
| Ions/Molecules | |
| Na+ | 5.198 |
| Cl− | −7.917 |
| $H_2PO_4^-$ | −3.736 |
| $HSO_4^-$ | −5.396 |
| Fluorescein | −3.000 |
| HEPES | −2.000 |
| Nucleic Acids | |
| DNA (in TAE) | −3.75 |
| DNA (in TBE) | −4.50 |
| Viruses | |
| HRV2 | −2.27 |
| HRV14 | −0.96 |
| HRV16 | −2.06 |
| HRV49 | −1.10 |
| Bacteria | |
| *Pseudomonas* sp. | −3.00 |
| *Alcaligenes euthropus* | −4.30 |
| *Methanobrevibacter smithii* | −2.70 |

In another approach, with reference to FIGS. 4A and 4B, a method includes co-feeding fluids (LE, $S_1$, $S_2$, $S_3$, DNA/RNA, BIO, TE, etc.) to a channel 402. The fluids may be co-fed in many different combinations and order of introduction, and the representation in FIG. 4A is not meant to be limiting in any way as to how the fluids may be introduced to the channel 402. The fluids comprise a leading electrolyte LE, a trailing electrolyte TE, biological objects BIO, at least one of DNA and RNA (DNA/RNA), and a spacer electrolyte $S_3$ having an electrophoretic mobility that is between an electrophoretic mobility (such as an average, mean, measured, lowest, highest, etc., electrophoretic mobility) of at least some of the biological objects BIO and an electrophoretic mobility (such as an average, mean, measured, lowest, highest, etc., electrophoretic mobility) of the at least one of the DNA and the RNA (DNA/RNA).

Of course, there may be more biological objects, nucleic acids, solvents, common and/or separate carriers, etc., present in the fluids in addition to the specific objects desired to be separated. For example, there may be many biological objects in the BIO fluid, additional nucleic acids in the DNA//RNA fluid, carriers in the leading and trailing electrolytes LE/TE, etc., and only a portion thereof may be desired to be separated. In this instance, a spacer electrolyte, such as spacer electrolyte $S_3$ may be used that has an electrophoretic mobility between that of the DNA/RNA and the desired. BIO, disregarding the electrophoretic mobility of the remainder of the biological objects. Other techniques may also be used to aid in the separation of desired and undesired objects in the fluids, and this example is not meant to be limiting in any manner.

As shown in FIG. 4B, an electric field (E) is applied to the fluids (LE, $S_1$, $S_2$, $S_3$, DNA/RNA, BIO, TE, etc.) in a direction perpendicular to an axis of the channel 402 (i.e., the direction of flow through the channel, as indicated by the Flow Direction Arrow) for inducing transverse isotachophoresis (ITP).

In some approaches, the channel 402 may be a capillary, a microchip, a microchannel, etc. Using an ITP protocol where a boundary between the leading electrolyte LE and mixture of the trailing electrolyte TE and nucleic acids DNA/RNA may be formed in a channel 402. Electrophoretic mobilities of nucleic acids DNA/RNA are generally smaller than that of the leading electrolyte LE, and larger than that of the trailing electrolyte TE. Therefore, the DNA and/or RNA may be spatially confined and separated from other analytes in the sample fluids.

In another embodiment, one or more spacer electrolytes $S_1$, $S_2$, $S_3$, etc., may be introduced to further separate nucleic acids DNA and/or RNA from other sample ions or biologicals BIO (e.g., viruses, bacteria, etc.). Electrophoretic mobilities of spacer ions may be in between that of nucleic acids DNA and/or RNA and that of target sample analytes, and may be smaller than that of the leading electrolyte LE, and larger than that of the trailing electrolyte TE. The spacer regions improve the nucleic acid DNA and/or RNA recover and extraction efficiencies.

According to preferred approaches, the trailing electrolyte TE may be co-fed to the channel 402 in a mixture with the at least one of the DNA and the RNA (DNA/RNA), as shown in FIG. 4A. In alternative embodiments, the trailing electrolyte TE may be co-fed to the channel 402 separately from the fluid having the at least one of the DNA and the RNA (DNA/RNA).

Also, in some embodiments, the fluids (LE, $S_1$, $S_2$, $S_3$, DNA/RNA, BIO, TE, etc.) may be co-fed to the channel 402 under a pressure higher than atmospheric pressure, such as to create a pressure gradient across the fluids as they flow. In addition, this pressure gradient may cause, at least in part, the fluids to flow from a condition of higher pressure, toward a condition of lower pressure. An alternative method to create this pressure gradient is to apply a vacuum to the outlet(s) of the channel 402, the outlet(s) being downstream from one or more inlet(s). Of course, any other method of forming this pressure gradient may also be used, and these examples are not meant to be limiting.

According to some embodiments, a bulk of the leading electrolyte LE may be spatially separated from the DNA and/or the RNA (DNA/RNA) upon introduction thereof to the channel 402, as shown in FIG. 4A. For example, more than about 50% of the leading electrolyte LE may be in a remote proximity from the DNA and/or the RNA (DNA/RNA). Of course, as the fluids flow in the channel 402, this spatial separation may be reduced and/or improved, depending upon processing and channel conditions in the flow direction.

In some more approaches, the method may include co-feeding a first spacer electrolyte, such as $S_1$, having an electrophoretic mobility that is between an electrophoretic mobility of the leading electrolyte LE and an electrophoretic mobility (such as an average, mean, measured, lowest, highest, etc., electrophoretic mobility) of the DNA and/or the RNA (DNA/RNA) and co-feeding a second spacer electrolyte, such as $S_2$ and/or $S_3$, having an electrophoretic mobility that is between an electrophoretic mobility of the trailing electrolyte TE and the electrophoretic mobility (such as an average, mean, measured, lowest, highest, etc., electrophoretic mobility) of the DNA and/or the RNA. In this way, the leading electrolyte LE may be more easily separated from the DNA and/or RNA (DNA/RNA), and the trailing electrolyte TE may be more easily separated from the DNA and/or RNA (DNA/RNA).

The biological objects BIO, in some approaches, may be selected from a group consisting of viruses, bacteria, and cells. Of course, other biological objects may also be used in conjunction with the methods described herein.

Many of the embodiments disclosed herein may be useful for purification of, separation of, and/or identification of harmful and/or rapidly spreading viral-like particles from biological samples. Of particular usefulness may be the implementation of the methods disclosed herein in sample preparation steps prior to analysis of nucleic acids (polymerase chain reaction (PCR), gel-electrophoresis, DNA sequencing, etc.) or to remove nucleic acids from sample fluids to be analyzed which may interfere with the analysis thereof.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method, comprising:
    co-feeding fluids comprising a leading electrolyte, a trailing electrolyte, at least one protein and at least one of DNA and RNA to a channel;
    applying an electric field to the fluids in a direction perpendicular to an axis of the channel for inducing transverse isotachophoresis; and
    acoustically focusing one or more of the leading electrolyte, the trailing electrolyte, the at least one protein, the DNA, the RNA,
    wherein the trailing electrolyte is co-fed to the channel in a mixture with the at least one protein and the at least one of DNA and RNA.

2. The method of claim 1, wherein either the leading electrolyte is co-fed to the channel in a mixture with a spacer electrolyte; or the trailing electrolyte is co-fed to the channel separately from the at least one of DNA and RNA.

3. The method of claim 1, further comprising generating a pressure gradient across the fluids as the fluids flow.

4. The method of claim 3, wherein generating the pressure gradient comprises one or more of:
    co-feeding the fluids under an amount of pressure higher than atmospheric pressure applying a vacuum to the channel; and
    applying a gravitational force to the fluids in the channel.

5. The method of claim 1, further comprising applying a vacuum to an outlet of the channel.

6. The method of claim 1, further comprising co-feeding a spacer electrolyte having an electrophoretic mobility that is between an electrophoretic mobility of the leading electrolyte and an electrophoretic mobility of the at least one protein and the at least one of the DNA and the RNA.

7. The method of claim 1, further comprising co-feeding a spacer electrolyte having an electrophoretic mobility that is between an electrophoretic mobility of the trailing electrolyte and an electrophoretic mobility of at least one of the at least one protein and the at least one of the DNA and the RNA, and
    wherein the spacer electrolyte is fed to the channel in a mixture with the leading electrolyte.

8. The method of claim 1, further comprising:
    co-feeding a first spacer electrolyte having an electrophoretic mobility that is between an electrophoretic mobility of the leading electrolyte and an electrophoretic mobility of the at least one protein and the at least one of the DNA and the RNA; and co-feeding a second spacer electrolyte having an electrophoretic mobility that is between an electrophoretic mobility of the trailing electrolyte and the electrophoretic mobility of the at least one protein and the at least one of the DNA and the RNA.

9. The method of claim 1, further comprising co-feeding a spacer electrolyte having an electrophoretic mobility that is between an electrophoretic mobility of biological objects in one of the fluids and an electrophoretic mobility of the at least one of the at least one protein and the DNA and the RNA,
wherein the biological objects are selected from a group consisting of viruses, bacteria, and cells.

10. The method of claim 1, further comprising:
co-feeding a first spacer electrolyte having an electrophoretic mobility that is between an electrophoretic mobility of the leading electrolyte and an electrophoretic mobility of the at least one protein and the at least one of the DNA and the RNA;
co-feeding a second spacer electrolyte having an electrophoretic mobility that is between an electrophoretic mobility of the trailing electrolyte and the electrophoretic mobility of the at least one protein and the at least one of the DNA and the RNA; and
co-feeding a third spacer electrolyte having an electrophoretic mobility that is between an electrophoretic mobility of at least some biological objects in one of the fluids and the electrophoretic mobility of the at least one protein and the at least one of the DNA and the RNA.

11. The method as recited in claim 10, further comprising:
separating the leading electrolyte, the trailing electrolyte, the at least one protein, the at least one of the DNA and the RNA, the first spacer electrolyte, the second spacer electrolyte, and the third spacer electrolyte into individual fluid flows within the channel; and
extracting, via a plurality of outlets, each of the leading electrolyte, the trailing electrolyte, the at least one protein, the at least one of the DNA and the RNA, the first spacer electrolyte, the second spacer electrolyte, and the third spacer electrolyte from each of the individual fluid flows within the channel,
wherein the leading electrolyte, the trailing electrolyte, the at least one protein, the at least one of the DNA and the RNA, the first spacer electrolyte, the second spacer electrolyte, and the third spacer electrolyte are co-fed to the channel in a mixture.

12. A method, comprising:
co-feeding fluids to a channel, the fluids comprising:
a leading electrolyte;
a trailing electrolyte;
biological objects;
DNA and RNA, wherein the trailing electrolyte is co-fed to the channel in a mixture with the DNA and the RNA; and
a spacer electrolyte having an electrophoretic mobility that is between an electrophoretic mobility of at least some of the biological objects and an electrophoretic mobility of the DNA and the RNA; and
applying an electric field to the fluids in a direction perpendicular to an axis of the channel for inducing transverse isotachophoresis;
acoustically focusing one or more of the leading electrolyte, the trailing electrolyte, the biological objects, the DNA and the RNA, and the spacer electrolyte;
separating the leading electrolyte, the trailing electrolyte, the biological objects, the DNA and the RNA, and the spacer electrolyte into individual fluid flows within the channel; and
extracting, via a plurality of outlets, each of the leading electrolyte, the trailing electrolyte, the biological objects, the DNA and the RNA, and the spacer electrolyte from each of the individual fluid flows within the channel.

13. The method of claim 12, wherein the leading electrolyte is co-fed to the channel in a mixture with the spacer electrolyte.

14. The method of claim 12, wherein the fluids are fed to the channel as a mixture under an amount of pressure higher than atmospheric pressure.

15. The method of claim 12, wherein the spacer electrolyte is fed to the channel in a mixture with the leading electrolyte.

16. The method of claim 12, wherein a bulk of the leading electrolyte is spatially separated from the DNA and the RNA upon introduction thereof to the channel.

17. The method of claim 12, the fluids fu her comprising one or more of:
a first spacer electrolyte having an electrophoretic mobility that is between an electrophoretic mobility of the leading electrolyte and the electrophoretic mobility of the DNA and the RNA; and
a second spacer electrolyte having an electrophoretic mobility that is between an electrophoretic mobility of the trailing electrolyte and the electrophoretic mobility of the DNA and the RNA, and
wherein the fluids are fed to the channel as a mixture.

18. The method of claim 12, further comprising generating a pressure gradient across the fluids as the fluids flow, wherein generating the pressure gradient comprises one or more of:
co-feeding the fluids under an amount of pressure higher than atmospheric pressure;
applying a vacuum to the channel; and
applying a gravitational force to the fluids in the channel.

19. The method of claim 12, the fluids further comprising;
co-feeding a first spacer electrolyte having electrophoretic mobility that is between an electrophoretic mobility of the leading electrolyte and the electrophoretic mobility of the DNA and the RNA; and
co-feeding a second spacer electrolyte having electrophoretic mobility that is between an electrophoretic mobility of the trailing electrolyte and the electrophoretic mobility of the DNA and the RNA, and
wherein the fluids are fed to the channel as a mixture.

20. A method, comprising:
co-feeding fluids to a channel via an inlet, the fluids comprising:
a leading electrolyte;
a trailing electrolyte;
at least one biological object;
at least one of DNA and RNA;
a first spacer electrolyte having an electrophoretic mobility that is between an electrophoretic mobility of the leading electrolyte and an electrophoretic mobility of the at least one protein and the at least one of the DNA and the RNA;
a second spacer electrolyte having an electrophoretic mobility that is between an electrophoretic mobility of the trailing electrolyte and the electrophoretic mobility of the at least one protein and the at least one of the DNA and the RNA; and
a third spacer electrolyte having an electrophoretic mobility that is between an electrophoretic mobility of at least one biological object in one of the fluids and the electrophoretic mobility of the at least one biological object and the at least one of the DNA and the RNA;

generating a pressure gradient across the fluids as the fluids flow;

applying an electric field to the fluids in a direction perpendicular to an axis of the channel;

acoustically focusing one or more of the leading electrolyte, the trailing electrolyte, the at least one biological object, the at least one of the DNA and the RNA, the first spacer electrolyte, the second spacer electrolyte, and the third spacer electrolyte;

separating the leading electrolyte, the trailing electrolyte, the at least one biological object, the at least one of the DNA and the RNA, the first spacer electrolyte, the second spacer electrolyte, and the third spacer electrolyte into individual fluid flows within the channel; and extracting, via a plurality of outlets, each of the leading electrolyte, the trailing electrolyte, the at least one biological object, the at least one of the DNA and the RNA, the first spacer electrolyte, the second spacer electrolyte, and the third spacer electrolyte from each of the individual fluid flows within the channel;

wherein the fluids are co-fed to the channel under an amount of pressure higher than atmospheric pressure, wherein the fluids are co-fed to the channel in a mixture, and wherein the pressure gradient is generated via selective application of one or more of a vacuum and gravity.

* * * * *